March 26, 1957 A. KRAMER Plant Pat. 1,583
CAMELLIA PLANT
Filed June 6, 1956
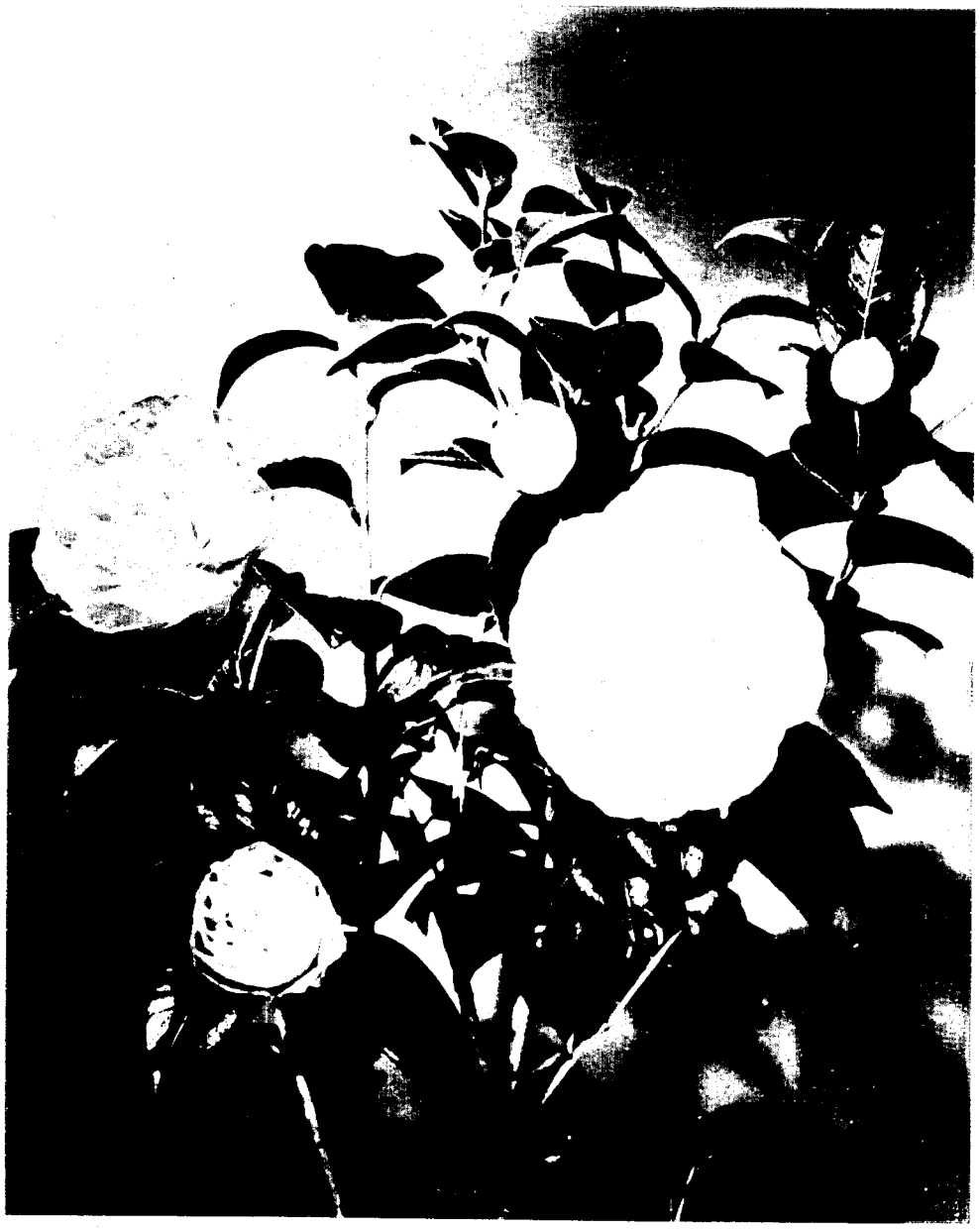
Inventor.
August Kramer
By: Robb & Robb
Attorneys.

United States Patent Office

Plant Pat. 1,583

Patented Mar. 26, 1957

1,583

CAMELLIA PLANT

August Kramer, Ontario, Calif., assignor to Kramer Bros. Nurseries, Upland, Calif., a partnership Application June 6, 1956, Serial No. 589,840

1 Claim. (Cl. 47—69)

The present invention relates to a new and distinct variety of camellia plant which originated as a seedling of the variety known as "Princess Bacciochi" (unpatented).

In the course of my nursery operations devoted to the production and cultivation of various camellia varieties, I planted some seeds of various varieties, including seeds of the variety "Princess Bacciochi" referred to above. Among the resulting seedlings, my attention was attracted to one particular seedling by virtue of the vigorous and erect growth of the plant, and the large size and rich color of the blooms. On closer inspection, I found that this seedling was in the group derived from seeds of the "Princess Bacciochi" variety, but was substantially different from the latter in a number of important respects. Thereupon, I promptly took steps to asexually reproduce the new seedling to ascertain the transmissibility of the improved characteristics thereof by asexual reproduction. Such asexual reproduction, as performed by me in my nursery at Upland, California, by both cuttings and graftings have conclusively demonstrated that the aforementioned seedling is definitely differentiated from the variety "Princess Bacciochi," as well as from all other varieties of which I am aware, and that the following outstanding characteristics come true to form and are established and transmissible through succeeding propagations:

(1) A vigorous and upright habit of plant growth;

(2) The large, sharply serrated, elliptical and pointed-tipped form of the leaves;

(3) The large flowers of loose, double-peony form;

(4) Thick, broad-obovate outer flower petals of good substance, with smaller center petals and petaloids of irregular form, but arranged in a rounded mass about the ovary;

(5) A strong adherence of the flower to the receptacle, and their good keeping qualities on the plant and as cut flowers; and (6) The distinctive Turkey Red general color tonality of the flowers.

The accompanying drawing shows typical specimens of the vegetative growth and flowers of my new camellia variety in different stages of development and as depicted in color as nearly true as it is reasonably possible to make the same in a color illustration of this character.

The following is a detailed description of my new variety, with color terminology in accordance with the Horticultural Color Chart of the British Color Council, except where general color terms of ordinary dictionary significance are obvious:

Parentage: Seedling of "Princess Bacciochi."

Propagation: Holds its distinguishing characteristics through successive propagations by both cuttings and graftings.

*Flower*

Locality where grown and observed: Upland, California.

Blooming habit: Mid-season; late January and February.

Bud:

*Size.*—Large.

*Form.*—Sub-globular.

*Sepals.*—Rounded apices; silky; shallow; cupped; with narrow brown margins. Color: outer surface—grayish green; inner surface—silvery gray.

Bloom:

*Size (when fully open).*—Large; from 4½ to 5½ inches.

*Borne.*—Sometimes singly and sometimes 2 or 3 to a stem; on normal stems.

*Form.*—When first petal opens—flat peony form. When fully opened—round peony form.

*Petalage.*—Irregular-double; folded and incomplete petals and large petaloids intermixed with stamens form multi-centered flower.

*Color.*—Turkey Red, Plate 721/1.

Petals: Firm substance; with 10 to 12 guards; thick; leathery; shiny.

*Shape.*—Near orbicular; with entire margins and rounded apices; with medium long and tapered hafts.

*Arrangement.*—Irregular.

*Lasting quality.*—On the plant—keeps well; corolla does not readily separate from stem and calyx. As cut flower—keeps well.

*Genital organs*

Stamens, anthers: Few; small.

*Color.*—Buttercup Yellow, Plate 5/1.

*Arrangement.*—Irregular; interspersed with petals.

Stamens, filaments: Medium length; united for half their length. Color—white at tips and pinkish at base.

*Plant*

Growth: Vigorous; upright; fast-growing; densely foliaged.

Foliage:

*Size.*—Large.

*Length.*—Up to 10 cm.

*Width.*—Up to 6 cm.

*Quantity.*—Normal.

*Color.*—Upper surface—Glossy Spinach Green, Plate 0960. Under surface—glossy lighter green.

*Shape.*—From ovate to broad-elliptic; from medium long-pointed to tapering.

*Texture.*—Heavy; leathery; glossy.

*Petioles.*—Stout; up to 1 cm. long.

*Ribs and veins.*—Prominent on face; noticeable beneath.

*Edge.*—Broadly and coarsely serrated.

I claim:

A new and distinct variety of camellia plant, substantially as herein shown and described, characterized particularly as to novelty by its vigorous and upright habits of growth, its large, sharply serrated, elliptical and pointed-tipped leaves, its large flowers of loose, double-peony form, its thick, broad-obovate outer flower petals of good substance and smaller center petals and petaloids of irregular form but arranged in a rounded mass about the ovary, the strong adherence of its flowers to their receptacles, the good keeping qualities of its flowers both on the plant and as cut flowers, and the distinctive Turkey Red general color tonality of its flowers.

No references cited.